United States Patent [19]
Cullinan

[11] Patent Number: 5,550,151
[45] Date of Patent: Aug. 27, 1996

[54] METHODS OF REDUCING SCARRING IN WOUND HEALING

[75] Inventor: George J. Cullinan, Trafalgar, Ind.

[73] Assignee: Eli Lilly Company, Indianapolis, Ind.

[21] Appl. No.: 293,851

[22] Filed: Aug. 22, 1994

[51] Int. Cl.$^6$ ................................................. A61K 31/38
[52] U.S. Cl. ............................................................ 514/445
[58] Field of Search .............................................. 514/445

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

| | | |
|---|---|---|
| WO93/10113 | 5/1993 | WIPO . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Black et al., "Uterine Bioassay of Tamoxifen, Trioxifene, and New Estrogen Antagonist (LY117018) in Rats and Mice," Life Sciences, 26: 1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanism," Endocrinology 109;1981, 987–989.
Black, L. J. "Biological Actions and Binding Properites of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H–LY139481 Distribution in Vivo. Sixty–fifth Annual Meeting of the Endocrine Society, San Antonio, Texas, Jun. 8–10, 1983, abs. 93.
Black et al., Antagonism of Estrogen Action with a New benzothiopene Derived Antiestrogen, Life Sciences, 32:1983. 1031–1036.
Black et al., The Relationship of the Antiestrogenic Efficacy of LY156758 to its Pharmocokinetics and Metabolism Following Oral Administration to Adult Ovariectomized Rats, Seventh International Congress of Endocrinology, Quebec City, Canada, Jul. 1–7, 1984, abs. 323.
112CA:701964 Neubauer et al., 1990.

*Primary Examiner*—Russell Travers
*Attorney, Agent, or Firm*—James J. Sales; David E. Boone

[57] ABSTRACT

A method of inhibiting scarring comprising administering to a human in need thereof an effective amount of a compound having the formula

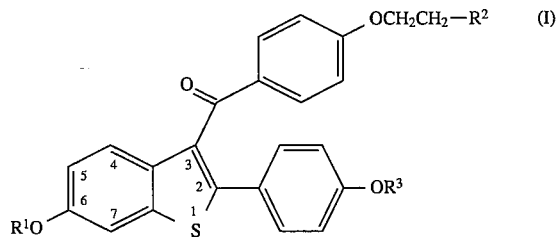

wherein $R^1$ and $R^3$ are independently hydrogen,

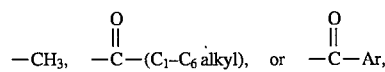

wherein Ar is optionally substituted phenyl;

$R^2$ is selected from the group consisting of pyrrolidine, hexamethyleneamino, and piperidino; or a pharmaceutically acceptable salt or solvate thereof.

3 Claims, No Drawings

METHODS OF REDUCING SCARRING IN WOUND HEALING

BACKGROUND OF THE INVENTION

A scar can be defined as an abnormal deposition of fibrous components, mostly matrix products such as collagen and fibronectin, at the site of injury. This deposition of fibrous tissue is in extreme abundance in comparison to normal skin. The result of this deposition is the granular surface or "lumpiness", which one would usually recognize as scar tissue. Besides its visual difference compared to normal skin, scar tissue also differs from normal skin in its biomechanical properties. Scar tissue, like other highly fibrous tissue, is less pliable and usually weaker in tensile strength. It is this loss of pliability and weakness which usually leads to the tissue's loss of function. For example, scarring of the hand, especially near joints, often leads to restricted movement, since the scarred skin can not stretch with the movement of the joint. Similarly, a scarred heart valve will be less strong and more prone to failure with a decrease in its tensile strength. (For a further discussion, see: Andrew's Diseases of the Skin, Domonkos, A. N., et al., W. B. Saunders Co., 1982, p. 18–19.)

The production of scar tissue as a sequelae of the healing of wounds or trauma is well known and many times thought to be an inevitable consequence of the healing process. In many cases, the scar tissue formed during the healing process is not a matter of great concern either medically or socially. However, there are abundant cases where the production of scar tissue is both of medical and social consequence to the individual. In cases when the initiating trauma to the patient involves areas of the body which are exposed to public view such as the face, arms or neck, scar formation can have lasting physiological and social implications to the patient. The physiological impact of a disfiguring facial scar due some traumatic event can in some people be devastating or at least discomforting depending on the severity of the disfigurement and the physiological makeup of the individual. In certain cases, a disfiguring scar can have not only a social stigma associated with it, but also an economic loss in those cases where personal appearances are an important attribute. Manytimes, it is often necessary or desirable to have reconstructive surgery to remove scar tissue for appearance sake. This necessity for surgery is a costly process in terms of economics as well as the pain and suffering which the patient must endure. It would be great benefit if there were a treatment available which would obviate the need for reconstructive surgery.

Additionally, there are cases where the formation of scar tissue from the healing process of a trauma has medical consequences apart from the potential unsightliness of scar formation. In these cases, the formation of scar tissue can inhibit the normal physiological function of a tissue to perform its normal role. Such an example would be the case of wide spread scarring such as that seen in severe burn cases. Patients who survived and have recovered from wide spread burns or who experienced burns in critical areas such as the hands or face, often have scar tissue which greatly decreases their ability regain normal movement and function of the affected areas. Such cases often require repeated surgery to allow the patient to regain function of the affected area and in many cases this reconstructive surgery is only partially effective, leaving the patient with some degree of permanent disability. Such a loss of tissue function can also be seen in cases where the trauma has been internal. The causes of internal trauma may originate from external sources such as puncture wounds or may be the inadvertent consequences of a beneficial surgical intervention such heart, vascular, neuro, or muscular operations. Regardless of cause, the formation of internal scar tissue can impair normal function. It would be of great medical benefit to have an agent which reduce the formation of scar tissue during the normal healing process.

Currently, there is no systemic agent which has shown to be efficacious in reducing the formation of scar tissue in humans. Surgical techniques and special wound dressings have been partially successful in reducing many cases of scar formation. However, these techniques may not be practical in cases where the damage is either wide-spread, such as burns, or impractical due to internal location.

Conditions which lead to scar formation as opposed to normal wound healing are poorly understood; however, there appears to be a link between the number, type, and duration of residence of inflammatory cells and the formation of scar tissue. Large influxes of inflammatory cells, especially macrophages, appear to promote the formation of scar tissue. Cytokines produced at the site of trauma have been implicated as factors in controlling the influx of inflammatory cells and hence, controlling the potential of scarring. In particulars a recent report in the literature by Shah et al., Lancet, 1992; 339: 213–214, implicates Transforming Growth Factor B (TGF-$\beta$) as being a key cytokine which exacerbates scar formation a experimental, animal model of scarring.

TGF-$\beta$ is a peptide growth factor which refers to a generic family of peptides, often called isoforms meaning that members of the family either share amino acid homology and/or have similar physiological actions. Of particular interest to the subject of wound healing are: TGF-$\beta$s 1, 2, and 3. For further discussion of the TGF-$\beta$ family of peptides, the subject is reviewed in Roberts A. B. and Sporn M. B., "The Transforming Growth Factor-$\beta$s.", Sporn and Roberts, eds; "Peptide Growth Factors and Their Receptors I". Berlin, Springer Verlag, 1990 419–472. Additionally, TGF-$\beta$s in wound healing, references in Ferguson, ibid., are germane.

Very recently, the literature reports that different isoforms of TGF-$\beta$ have different effects on scar formation. It has been demonstrated in experimental, animal scar models that TGF-$\beta$1 appears to exacerbate the formation of scar tissue. However, it was shown that TGF-$\beta$3 protected the skin from scar formation and allowed normal healing of the wound. The proposed mechanism for this action of TGF-$\beta$3 was the decrease in macrophage and monocyte infiltration at the wound site. Ferguson, M. W., "Wound Healing, Scarring, TGF-$\beta$ antagonists and Isoforms," Abst. NIH TGF-$\beta$ Symposia, Bethesda Md., May 3, 1994.

SUMMARY OF THE INVENTION

This invention provides methods of inhibiting scarring comprising administering to a human in need thereof an effective amount of a compound of formula I

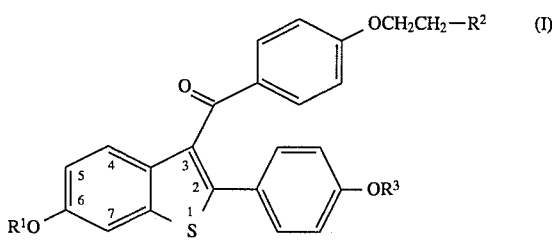

wherein $R^1$ and $R^3$ are independently hydrogen,

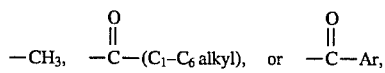

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting scarring. Specifically, the method comprises administering an effective amount of a compound of formula I to a wound site for a period of time sufficient to minimize the scar, or to prevent the formation of a hypertrophic scar.

The therapeutic and prophylactic treatments provided by this invention are practiced by administering to a human in need thereof a dose of a compound of formula I or a pharmaceutically acceptable salt or solvate thereof, that is effective to inhibit scarring, especially in wound healing.

The term "inhibit" includes its generally accepted meaning which includes prohibiting, preventing, restraining, and slowing, minimizing, stopping or reversing progression, severity or a resultant symptom. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, ointments, salves, cremes, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

For topical administration, the compounds may be formulated as is known in the art for direct application to an area. Conventional forms for this purpose include ointments, lotions, pastes, jellies, sprays, and aerosols. The percent by weight of a compound of the invention present in a topical formulation will depend on various factors, but generally will be from 0.5% to 95% of the total weight of the formulation, and typically 1–25% by weight.

The compositions can take the form of an aqueous or anhydrous solution or dispersion, or alternatively the form of an emulsion or suspension.

These compositions can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions can also contain thickening agents such as cellulose and/or cellulose derivatives. They can also contain gums such as xanthan, guar or carob gum or gum arabic, or alternatively polyethylene glycols, bentones and montmorillonites, and the like.

These compositions can also contain, in combination, other active agents such as retinoic derivatives, antibacterial agents, and anti-inflammatories. Examples of such agents include benzoyl peroxide, tetracyclins, erythromycin, minocycline, clindamycin, ampicillin, trimethoprim, sulfamethoxazole, vitamin A, and isotretinoin.

It is possible to add, if necessary, an adjuvant chosen from antioxidants, surfactants, other preservatives, film-forming, keratolytic or comedolytic agents, perfumes and colorings. For example, among antioxidants, t-butylhydroquinone, butylated hydroxyanisole, butylated hydroxytoluene and α-tocophrol and its derivatives may be mentioned.

The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

The method of administering an acceptable dose of the compound of formula I to inhibit scarring is dependent upon the location of the wound and the extent of scarring. In particular, a compound either alone or in combination with a pharmaceutically acceptable vehicle, can be topically applied to the surface of the wound site; it can be injected into the wound site; or it can be incorporated into a controlled release polymer and surgically implanted in a region to be treated. Surgical implantation is advantageous for treating disorders such as cirrhosis of the liver and constrictive pericarditis. This permits the compound to be localized in the diseased site without adversely affecting the patient or releasing excessive amounts of the drug into the circulation system.

The particular oral dosage of a compound of formula I required to inhibit scarring according to this invention will depend upon the severity of the condition, the route of administration, and related factors that will be decided by the attending physician. Generally, accepted and effective daily oral doses will be from about 0.1 to about 1000 mg/day, and more typically from about 50 to about 200 mg/day. Such dosages will be administered to a subject in need thereof from once to about three times each day, or more often as needed and for a sufficient duration, to effectively inhibit scarring.

It is usually preferred to administer a compound of formula I in the form of an acid addition salt, as is customary in the administration of pharmaceuticals bearing a basic group, such as the piperidino ring, For such purposes the following forms are available.

Formulations

In the formulations which follow, "Active ingredient" means a compound of formula I.

| Formulation 1: Gelatin Capsules Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Formulation 2: Raloxifene capsule | |
|---|---|
| Ingredient | Quantity (mg/capsule) |
| Raloxifene | 1 |
| Starch, NF | 112 |
| Starch flowable powder | 225.3 |
| Silicone fluid 350 centistokes | 1.7 |

| Formulation 3: Raloxifene capsule | |
|---|---|
| Ingredient | Quantity (mg/capsule) |
| Raloxifene | 5 |
| Starch, NF | 108 |
| Starch flowable powder | 225.3 |
| Silicone fluid 350 centistokes | 1.7 |

| Formulation 4: Raloxifene capsule | |
|---|---|
| Ingredient | Quantity (mg/capsule) |
| Raloxifene | 10 |
| Starch, NF | 103 |

Formulation 4: Raloxifene capsule

| Ingredient | Quantity (mg/capsule) |
|---|---|
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following composition is prepared:

Formulation 9

| Ingredient | Quantity (mg/5 ml) |
|---|---|
| Hydroxypropylcellulose | 1.5 g |
| Active Ingredient | 1.5–30 g |
| Isopropanol qs | 100 g |

Formulation 10
The following composition is prepared:

| Ingredient | Quantity (mg/5 ml) |
|---|---|
| Hydroxypropylcellulose | 1.5 g |
| Ethyl lactate | 15.0 g |
| Active Ingredient | 1.5–30 g |
| Isopropanol qs | 100 g |

Formulation 11
The following composition is prepared:

| Ingredient | Quantity (mg/5 ml) |
|---|---|
| Hydroxypropylcellulose | 1.0 g |
| Butylated hydroxytoluene | 0.02 g |
| Active Ingredient | 1.5–25 g |
| Ethanol qs | 100 g |

Formulation 12
The following composition is prepared:

| Ingredient | Quantity (mg/5 ml) |
|---|---|
| Hydroxypropylcellulose | 1.5 g |
| Butylated hydroxytoluene | 0.01 g |
| $C_8$–$C_{12}$ fatty acid triglycerides | 10.0 g |
| Active Ingredient | 1.5–30 g |
| Isopropanol qs | 100 g |

Formulations 9–12 take the form of gels.

Formulation 13
The following composition is prepared:

| Ingredient | Quantity (mg/5 ml) |
|---|---|
| Isopropanol | 46.0 g |
| Active Ingredient | 1.0–15 g |
| $C_8$–$C_{12}$ fatty acid triglycerides | 49.0 g |

Formulation 14
The following composition is prepared:

| Ingredient | Quantity (mg/5 ml) |
| --- | --- |
| Ethanol | 69.0 g |
| Ethyl lactate | 10.0 g |
| Active Ingredient | 1.5–20 g |
| $C_8$–$C_{12}$ fatty acid triglycerides | 30.0 g |

Formulation 15
The following composition is prepared:

| Ingredient | Quantity (mg/5 ml) |
| --- | --- |
| Isopropanol | 47.0 g |
| Acetone | 10.0 g |
| Ethyl lactate | 10.0 g |
| Active Ingredient | 1–15 g |
| $C_8$–$C_{12}$ fatty acid triglycerides | 30.0 g |

Formulation 16
The following composition is prepared:

| Ingredient | Quantity (mg/5 ml) |
| --- | --- |
| Ethanol | 95.08 g |
| Butylated hydroxytoluene | 0.02 g |
| Active Ingredient | 1.5–25 g |

Formulation 17
The following composition is prepared:

| Ingredient | Quantity (mg/5 ml) |
| --- | --- |
| White vaseline | 50.0 g |
| Liquid paraffin | 15.0 g |
| Refined paraffin wax | 32.0 g |
| Active Ingredient | 1–20 g |

Formulation 18
The following composition is prepared:

| Ingredient | Quantity (mg/5 ml) |
| --- | --- |
| White vaseline | 50.0 g |
| Liquid paraffin | 13.0 g |
| Refined paraffin wax | 32.0 g |
| Active Ingredient | 1–20 g |

Formulations 17 and 18 takes the form of a stick.

ASSAYS

Assay 1

The adult rat as reported by Shah et al., "Control of Scarring in Adult Wounds by Neutralizing Antibody to Transforming Growth Factor β", *The Lancet*, 339, Jan. 25, 1992 is employed. Five to fifty adult male Sprague Dawley rats (200–250 g) are anaesthetized with halothane, nitrous oxide, and oxygen inhalation. Three incisions, 10 mm in length and to the depth of the panniculus carnosus, are made on the dorsal skin equidistant from the midline and adjacent to three limbs. The wounds are left unsutured to heal by secondary intention to produce the greatest amount of granulation tissue and scarring. In each animal, one wound (control) is unmanipulated, one (sham control) is injected with an irrelevant antibody (rabbit IgG), one (positive control) is injected with a compound of formula 1. Injections of 100 μl in phosphate-buffered saline were introduced into each wound daily on days 0–2. The fluid was infiltrated along the length of each wound margin through a single entry point 0.5 cm distal to the caudal end of the wound. At least 5 animals are killed by chloroform overdose on each of days 7, 14, 28, 42, 70 and 168 after wounding. The wounds are bisected for histology/immunocytochemistry and tensiometry or biochemical analysis. For each staining procedure sections from randomly chosen positions throughout each wound are analysed.

For tensiometry, one or more dumb-bell shaped strips are cut perpendicular to the long axis of each wound with a template, 0.3 cm wide at the centre (wound) and 3.0 cm long. The wound and surrounding normal skin are microdissected free from the underlying muscle and fat. The strips are cut from identical sites in all the wounds. Each strip is immediately extended to failure at 20 mm/min in an RDP Howden tensile testing instrument with a 500N load cell. The thickness of the wound is measured with a micrometer.

For biochemical analysis, individual wounds or normal skin samples are carefully microdissected free from the underlying fat and muscle, rapidly frozen, and lyophilised. The dried samples are weighed and the hydroxyproline content measured and the amount of collagen is calculated by assuming that it contains 16.6% hydroxyproline.

Assay 2

Five to fifty patients are selected for the clinical study. The patients suffer from small lacerations or wounds but otherwise are in good general health. Because of the idiosyncratic and subjective nature of these disorders, the study has a placebo control group, i.e., the patients are divided into two groups, one of which receives a compound of formula 1 as the active agent and the other receives a placebo. Patients in the test group receive between 50–200 mg of the drug per day by the oral route. They continue this therapy for 1–3 months. Accurate records are kept as to the number and severity of the symptoms in both groups and at the end of the study these results are compared. The results are compared both between members of each group and also the results for each patient are compared to the symptoms reported by each patient before the study began.

Assay 3

Five to fifty patients are selected for the clinical study. The patients are to undergo surgery in approximately six weeks. Because of the idiosyncratic and subjective nature of these disorders, the study has a placebo control group, i.e., the patients are divided into two groups, one of which receives a compound of formula 1 as the active agent and the other receives a placebo, administration beginning approximately 6 weeks prior to surgery. Patients in the test group receive between 50–200 mg of the drug per day by the oral route. They continue this therapy for 2–4 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

I claim:

1. A method of inhibiting scarring comprising administering to a human in need thereof an effective amount of a compound having the formula

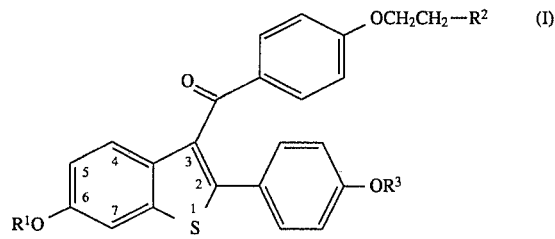

wherein $R^1$ and $R^3$ are independently hydrogen,

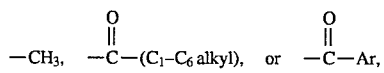

wherein Ar is optionally substituted phenyl;

$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

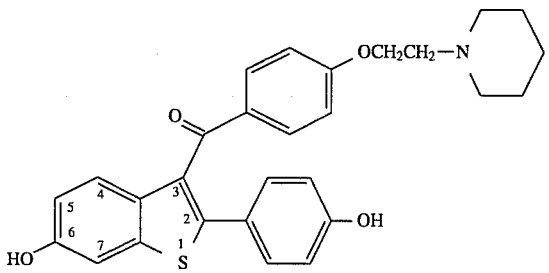

or its hydrochloride salt.

* * * * *